(12) United States Patent
Buge et al.

(10) Patent No.: US 11,234,931 B2
(45) Date of Patent: **\*Feb. 1, 2022**

(54) NO-RINSE CHEMICAL FOAM CONTAINING BRIMONIDINE, AND USE THEREOF IN THE TREATMENT OF ROSACEA

(71) Applicant: GALDERMA RESEARCH & DEVELOPMENT, Biot (FR)

(72) Inventors: Jean-Christophe Buge, Nice (FR); Karine Nadau-Fourcade, Villeneuve Loubet (FR)

(73) Assignee: GALDERMA RESEARCH & DEVELOPMENT, Biot (FR)

( \* ) Notice: Subject to any disclaimer, the term of this patent is extended or adjusted under 35 U.S.C. 154(b) by 0 days.

This patent is subject to a terminal disclaimer.

(21) Appl. No.: 15/763,884

(22) PCT Filed: Sep. 27, 2016

(86) PCT No.: PCT/EP2016/073010
§ 371 (c)(1),
(2) Date: Jun. 8, 2018

(87) PCT Pub. No.: WO2017/055293
PCT Pub. Date: Apr. 6, 2017

(65) Prior Publication Data
US 2019/0099369 A1    Apr. 4, 2019

(30) Foreign Application Priority Data
Sep. 29, 2015 (FR) ...................... 1559200

(51) Int. Cl.
| | |
|---|---|
| *A61K 9/12* | (2006.01) |
| *A61K 9/00* | (2006.01) |
| *A61K 31/498* | (2006.01) |
| *A61P 17/00* | (2006.01) |
| *A61K 45/06* | (2006.01) |
| *A61K 47/02* | (2006.01) |
| *A61K 47/12* | (2006.01) |

(52) U.S. Cl.
CPC .............. *A61K 9/122* (2013.01); *A61K 9/007* (2013.01); *A61K 9/0014* (2013.01); *A61K 31/498* (2013.01); *A61K 45/06* (2013.01); *A61K 47/02* (2013.01); *A61K 47/12* (2013.01); *A61P 17/00* (2018.01)

(58) Field of Classification Search
CPC ........ A61K 9/122; A61K 47/12; A61K 47/02; A61K 45/06; A61K 9/007; A61K 9/0014; A61K 31/498; A61P 17/00
See application file for complete search history.

(56) References Cited

U.S. PATENT DOCUMENTS

| | | |
|---|---|---|
| 5,952,372 A | 9/1999 | McDaniel |
| 6,133,310 A | 10/2000 | Parks |
| 6,177,092 B1 | 1/2001 | Lentini et al. |
| 6,649,186 B1 | 11/2003 | Robinson et al. |
| 2002/0061855 A1 | 5/2002 | Parks |
| 2004/0184992 A1 | 9/2004 | Abram |
| 2005/0123487 A1 | 6/2005 | Spadini et al. |
| 2007/0237724 A1 | 10/2007 | Abram et al. |
| 2009/0191248 A1 | 7/2009 | Hoffman et al. |
| 2009/0214628 A1 | 8/2009 | De Rijk et al. |
| 2010/0291160 A1 | 11/2010 | Carver et al. |
| 2011/0008267 A1 | 1/2011 | Arkin et al. |
| 2011/0236503 A1 | 9/2011 | Kalli |
| 2011/0311592 A1 | 12/2011 | Birbara |
| 2012/0114574 A1 | 5/2012 | Touitou |
| 2013/0244976 A1 | 9/2013 | Inamoto et al. |
| 2013/0317108 A1 | 11/2013 | At |
| 2013/0338230 A1 | 12/2013 | At |
| 2013/0338235 A1 | 12/2013 | At |
| 2014/0364504 A1 | 12/2014 | Uddin |
| 2015/0306124 A1 | 10/2015 | Manetta et al. |
| 2017/0172877 A1 | 6/2017 | Buge et al. |
| 2017/0172972 A1 | 6/2017 | Buge et al. |
| 2018/0064638 A1\* | 3/2018 | Tamarkin ............... A61K 47/44 |

FOREIGN PATENT DOCUMENTS

| | | |
|---|---|---|
| AU | 2014359194 A1 | 7/2016 |
| CN | 104382863 A | 3/2015 |
| DE | 10 2008 029 357 A1 | 12/2009 |
| EP | 1 043 023 A1 | 10/2000 |

(Continued)

OTHER PUBLICATIONS

International Search Report and English translation dated Dec. 2, 2016 corresponding to International Patent Application No. PCT/EP2016/073010, 5 pages.
Written Opinion of the International Searching Authority dated Dec. 2, 2016 corresponding to International Patent Application No. PCT/EP2016/073010, 5 pages.
Onset Therapeutics, LLC, "Benzefoam Ultra", Drug Information Online—Drugs.com, Apr. 3, 2011, XP002739766. 9 pages.
Wikimedia Commons; "Citric Acid Speciation" https://commons.wikimedia.org/wiki/File:Citric_acid_speciation.png; accessed Jan. 10, 2020 (Year: 2011).

(Continued)

*Primary Examiner* — Robert S Cabral
(74) *Attorney, Agent, or Firm* — Foley & Lardner LLP; Sunil Talapatra

(57) ABSTRACT

A self-foaming composition is described that includes brimonidine, for a no-rinse topical application. The composition can include: at least one intermediate composition B including a gas-generating agent; at least one intermediate composition A including an agent for activating the gas-generating agent; and brimonidine or one of the pharmaceutically acceptable salts thereof being present in at least one of the intermediate compositions A and B. Also described, is a kit or a single container including a plurality of compartments including such a composition.

33 Claims, 3 Drawing Sheets

(56) References Cited

FOREIGN PATENT DOCUMENTS

Figure 1:
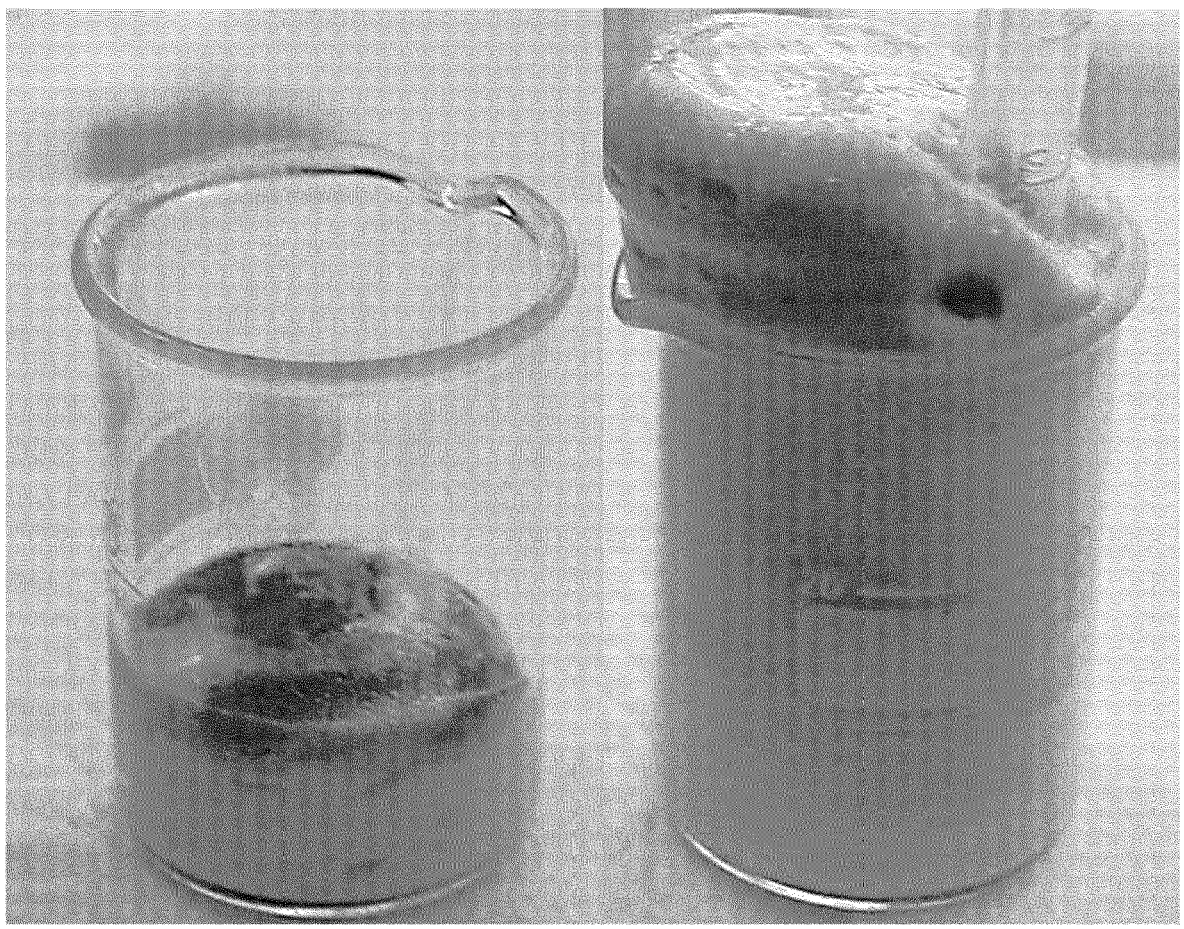

| | | |
|---|---|---|
| FR | 2761600 A1 | 10/1998 |
| FR | 2924944 A1 | 6/2009 |
| FR | 2943914 A1 | 10/2010 |
| JP | 2002-529391 A | 9/2002 |
| JP | 2004-217675 A | 8/2004 |
| JP | 2013-177460 A | 9/2013 |
| WO | 00/27356 A1 | 5/2000 |
| WO | WO-03/030664 A1 | 4/2003 |
| WO | WO-2004/037225 A2 | 5/2004 |
| WO | WO-2005/058272 A1 | 6/2005 |
| WO | WO-2009/069006 A2 | 6/2009 |
| WO | 2012/001065 A2 | 1/2012 |
| WO | WO-2012/085480 A1 | 6/2012 |
| WO | WO-2012/085481 A1 | 6/2012 |
| WO | WO-2012/085483 A1 | 6/2012 |
| WO | WO-2014/201541 A1 | 12/2014 |
| WO | WO-2015/082659 A1 | 6/2015 |

OTHER PUBLICATIONS

Holmes et al.: "Dermatological Adverse Events Associated with Topical Brimonidine Gel 0.33% in subjects with Erythema of Rosacea", Journal of Clinical and Aesthetic Dermatology, vol. 8, No. 8, Aug. 2015, 7 pages.

\* cited by examiner

NO-RINSE CHEMICAL FOAM CONTAINING BRIMONIDINE, AND USE THEREOF IN THE TREATMENT OF ROSACEA

CROSS-REFERENCE TO PRIOR APPLICATIONS

This application is a National Stage of PCT/EP2016/073010, filed Sep. 27, 2016, and designating the United States (published on Apr. 6, 2017, as WO 2017/055293 A1), which claims priority under 35 U.S.C. § 119 to French Application No. 1559200, filed Sep. 29, 2015, each hereby expressly incorporated by reference in its entirety and each assigned to the assignee hereof.

The present invention relates to a leave-on topical product in the form of a foam for the cosmetic or pharmaceutical treatment of the skin, comprising brimonidine in dissolved form. Brimonidine is an alpha-2 adrenergic receptor agonist indicated in the topical treatment of persistent facial erythema due to rosacea.

The term "brimonidine" refers to the molecule (5-bromo-quinoxalin-6-yl)(4,5-dihydro-1H-imidazol-2-yl)amine having the following structure:

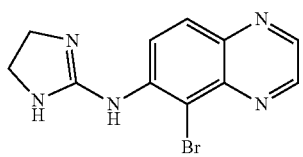 [SMILES: Brc1c(NC2=NCCN2)ccc2nccnc12]

Despite all the progress made, consumers are still in search of rapid and more practical compositions intended for topical application. Foams make it possible to overcome the problems of tolerance via better control of the dose, by means of their spreading properties and their low density.

Rosacea is a chronic inflammatory disease of facial skin which is occasionally conspicuous, and which may have a considerable impact on the life of the persons affected.

It is manifested by redness on the face, mainly on the forehead, the cheeks and the nose, accompanied by inflammatory spots (papules and pustules). Skin afflicted with rosacea tends to be very dry and sensitive.

Skin suffering from rosacea is very sensitive and very reactive skin. Rubbing the skin or washing it with hot water under the shower must be avoided. Mild alcohol-free and soap-free cleansing agents must be used, without rinsing, together with a suitable moisturizing cream.

In addition, some compounds used in compositions intended for a known topical application may result in side-effects that may limit the use and thus the effectiveness thereof. For example, some active principles have the major drawback of inducing irritation which may result in mediocre tolerance of the product. This may thus create, on the part of the patient, behavior of non-compliance with the treatment and of dissatisfaction regarding said treatment.

There is therefore a need to develop novel galenical forms that overcome the drawbacks mentioned previously in terms of tolerance, efficacy and compliance.

In this type of long-term pathology and for which the symptoms are treated without being able to eradicate the disease, there is thus a need for novel galenical forms in particular of foam type or foaming compositions which allow better control of the dose, in which brimonidine is soluble, stable, well-tolerated, efficient and pleasant to apply.

The composition according to the invention has the advantage of being in the form of a foam which is generated at the time of use and which is very well tolerated.

After its application, the composition according to the invention is not removed by rinsing.

One of the advantages of the composition of the invention is that it is particularly well tolerated, despite the fact that it is not removed by rinsing, as is shown by the examples illustrating one of the methods of evaluating the tolerance which are presented below.

Various methods exist for evaluating the tolerance of a pharmaceutical or cosmetic product for cutaneous use, among which may be mentioned the in vivo "in used" or "human patch test" test but also the in vitro test, such as the test for measurement of the irritation on Reconstructed Human Epidermis (RHE) described in the OECD TG 439 protocol. The latter method is described in detail in example 3.

Furthermore, the composition has the advantage of remaining on the surface of the skin and of delivering a smaller amount so as to prevent undesirable effects (rebound effect) and to obtain a foam that is suitable for treating rosacea.

The efficacy of an active principle and its adverse effects are associated with the penetration of the active agent through the skin. The formulary composition plays its fundamental role as a vehicle for the principle so that said principle reaches its therapeutic target. The release-permeation test described in example 5 on ex-vivo human skin highlights the advantage of applying a chemical foam containing brimonidine tartrate.

Foams or foaming compositions currently exist on the market. However, they all have a certain number of drawbacks:

This is because three types of foams or foaming compositions exist:

Aerosols, in which the foam is generated by a propellant gas but with the drawback of being aerosols having the well-known risks of the latter (contamination and breathing risks in particular).

Expanded creams, in which air bubbles are introduced into the product via a particular manufacturing process. This process has the drawback of being restricting at the industrial level and requires major capital expenditure with regard to the packaging equipment.

Foaming formulations which are low in foaming surfactants but packaged a packaging equipped with a mechanical foam-generating system (pump with grille of Pulvorex type). This type of formulation requires the use of foaming surfactants, which may lead to irritation in the case of leave-on products.

Thus, the need therefore remains to develop a pharmaceutical composition, the galenical form of which is different from the known galenical forms, in order, inter alia, to provide compositions intended for topical application containing brimonidine in solubilized form in well-tolerated compositions intended for topical application to human beings, in particular leave-on compositions (i.e. the composition is not removed by rinsing after it has been applied).

The aim of the present invention is thus to provide a composition which meets these needs.

The Applicant has thus developed a novel pharmaceutical composition intended for a leave-on topical application, which is in the form of a foam which advantageously does not contain any foaming surfactants. The term "foaming surfactant" defines surfactants which produce a voluminous, stable and creamy foam when they are mixed with water according to tests that are well known to those skilled in the art.

The following constitute foaming surfactants: anionic surfactants, cationic surfactants, amphoteric surfactants and nonionic surfactants of the family of alkylpolyglucosides and glucamides.

The galenical form according to the invention has the advantage of ensuring good solubility and good stability of brimonidine. Furthermore, this formulation advantageously results in the production of a mild foam which is fully tolerated and non-irritant, which allows better coverage of the area to be treated and which makes it possible to overcome the problems of tolerance by better control of the dose, by virtue of the spreading properties and the low density of the foam.

Finally, advantageously, this galenical form does not require, for the implementation thereof, the use of propellant gases or aerosols. Thus, "aerosol" or "spray" foams are excluded from the scope of the invention. Likewise, the foams of the prior art of expanded cream and/or foaming formulation type requiring a mechanical foam-generating system (Pulvorex type) are also excluded from the invention.

Finally, a subject of the present invention is the cosmetic use of the composition according to the invention, by topical application of this composition to the skin, and also a medicament intended for topical application to the skin, comprising such a composition.

The present invention will be described in greater detail in the description and the examples hereinbelow, and in the light of the figures attached to the present patent application.

FIG. 1 shows photographs of a first composition in accordance with the invention obtained by mixing the two intermediate compositions A5 placebo and B7 described in the examples, immediately after mixing them then when the reaction between these two compositions is complete (maximum foam volume).

Figure 2A:
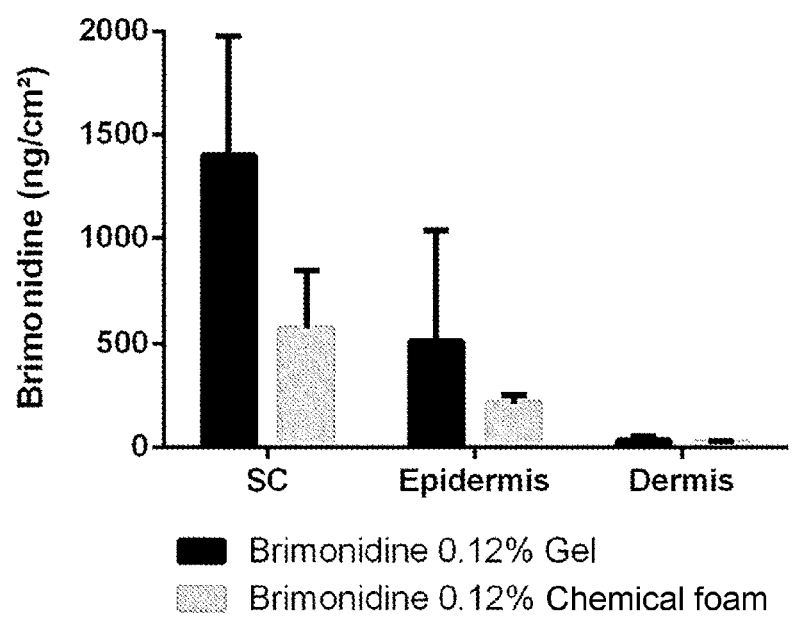
Figure 3A:
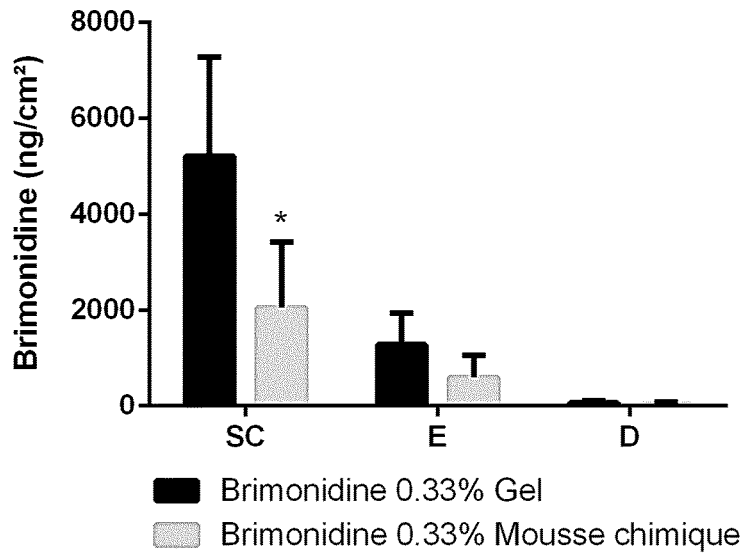

FIGS. 2A and 3A illustrate example 5 and represent the comparative results of penetration-permeation into the stratum corneum, the epidermis and the dermis of compositions in foam form according to the invention:
  a reference commercial composition containing 0.33% by weight of brimonidine in base form corresponding to 0.5% by weight of brimonidine tartrate;
  a reference in gel form containing 0.12% by weight of brimonidine in base form corresponding to 0.18% by weight of brimonidine tartrate;
  a whole foam formulation according to the invention containing 0.5% by weight of brimonidine tartrate composed of the mixture of compositions A3 and B7 described in example 1 (in a 50/50 weight ratio);
  a whole foam formulation according to the invention containing 0.18% by weight of brimonidine tartrate, composed of the mixture of compositions A4 and B7 described in example 1 (in a 50/50 weight ratio).

Figure 2B:
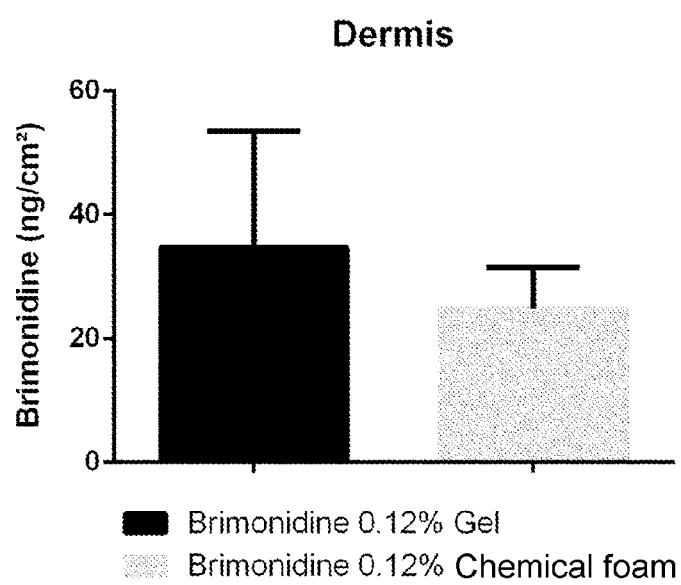
Figure 3B:
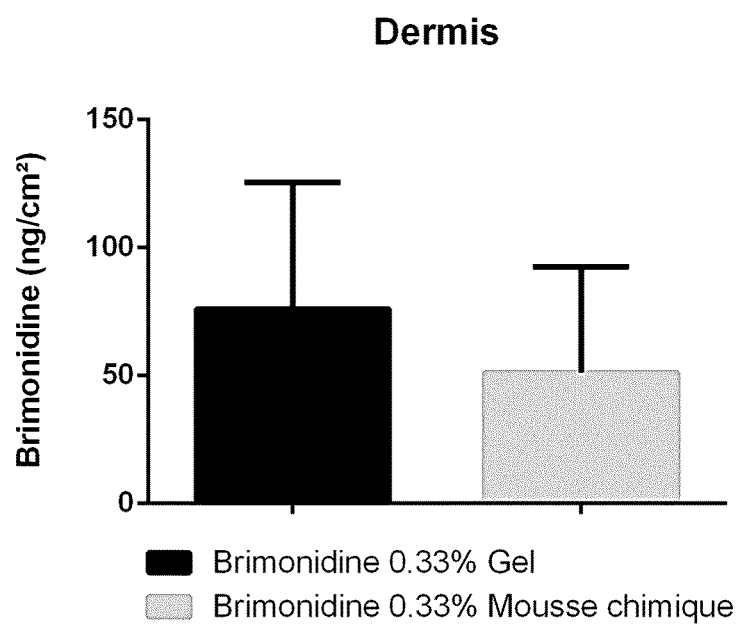

FIGS. 2B and 3B illustrate example 5 and represent the comparative results of penetration-permeation into the dermis on an enlarged scale of FIGS. 2A and 3A.

The composition according to the invention is capable of taking the form of a foam solely by virtue of its composition, and may also be defined as a self-foaming composition for topical application.

A first subject of the present invention is consequently a composition containing brimonidine, intended for leave-on topical application, which is provided in the form of a foam, advantageously of semisolid consistency, which advantageously does not contain any foaming surfactant and which comprises a medium that is pharmaceutically compatible with leave-on topical application, in particular to the skin and integuments.

The term "composition in the form of a foam" (also referred to hereinbelow as a self-foaming composition) means a composition of semisolid consistency having an aerated form comparable to a foam.

The self-foaming composition according to the present invention comprises two intermediate compositions or formulations in variable proportions and in particular the ingredients below:
  at least one intermediate composition or formulation A comprising an agent for activating the gas-generating agent mentioned below;
  at least one intermediate composition or formulation B comprising a gas-generating agent,
  brimonidine or a pharmaceutically acceptable salt thereof contained in at least one of said intermediate formulations A and B.

According to the invention, the composition is self-foaming, i.e. it foams by simple mixing of the intermediate compositions A and B. A subject of the invention is also the composition in foam form resulting from the mixing of said intermediate compositions A and B.

According to the invention, each intermediate composition (or formulation) may have a viscosity (measured at 25° C. and at atmospheric pressure) of between 1 cP and 500 000 cP, advantageously between 500 cP and 350 000 cP, measured with a conventional method of Brookfield RV DV-II type: spindle 6, speed 2.

According to the invention, the gas generated by the gas-generating agent may be any physiologically compatible gas which allows the production of a foam, for instance carbon dioxide ($CO_2$) or oxygen ($O_2$). Preferably, the gas generated from the gas-generating agent is carbon dioxide ($CO_2$).

According to the invention, since the gas concentration may vary, the amount of bubbles in the composition may vary and may thus give a composition which may range from not very aerated to very strongly aerated.

According to the invention, the term "agent for activating the gas-generating agent" means an ingredient which, by chemical reaction with the gas-generating agent, releases a gas. Preferentially, an acid/base reaction is involved.

Thus, according to the invention, the self-foaming composition may preferentially be in any form ranging from aerated to a highly expanded foam.

The composition according to the invention is suitable for topical application and may also comprise a physiologically acceptable medium, i.e. a medium that is compatible with the skin and integuments. It is preferably a pharmaceutically acceptable medium.

In addition, the composition may comprise any active agent that may have activity, optionally therapeutic activity. These active agents may be chosen, inter alia, from emollients, humectants, free-radical scavengers, anti-inflammatory agents, vitamins, depigmenting agents, antiacne agents, antiseborrheic agents, antifungal agents, keratolytic agents, sunscreens, slimming agents and skin-coloring agents.

According to the invention, the composition in foam form (i.e. ready to be applied) may have a pH of between 2 and 8, preferentially between 4 and 7.

Insofar as the intermediate composition(s) (or formulation(s)) require storage in at least two compartments for reasons of stability of the ingredients, the present invention relates either to a single compartmentalized container (each compartment receiving one intermediate formulation) and preferably comprising two or three compartments, or to a kit comprising each intermediate formulation stored independently from each other and physically separated.

Intimate extemporaneous mixing (directly on the skin or on any other support) of the intermediate formulations makes it possible to obtain the composition in foam form according to the invention.

More specifically, the intermediate composition (or formulation) A may be in the form of a solution, an emulsion (lotion, cream, emulsifier-free cream, milk or fluid cream) or a gel. This composition advantageously contains the agent for activating the gas-generating agent, preferentially an acid, in a sufficient amount (which may be in the form of an acid/base buffer at acidic pH), which may be, as a nonlimiting example, the citric acid/sodium citrate pair.

Formulation B may be in the form of a solution, a gel or an emulsion (lotion, cream, emulsifier-free cream, milk or fluid cream). This composition advantageously contains, in a sufficient amount, a gas-generating agent which may in particular be sodium bicarbonate.

Thus, a subject of the invention is also a kit or a single multi-compartment container as defined previously, for the extemporaneous preparation of a composition in foam form according to the invention, separately comprising at least two intermediate formulations (or intermediate compositions):
- an intermediate formulation A comprising at least one agent for activating the gas-generating agent; and
- an intermediate formulation B comprising at least one gas-generating agent;
- brimonidine or a pharmaceutically acceptable salt thereof being contained in at least one of said intermediate formulations A and B.

Brimonidine is preferably contained in intermediate composition A.

Gas-Activating Agent:

The agent for activating the gas-generating agent (also referred to as the "gas-activating agent") is a compound which reacts with the gas-generating agent via a chemical reaction (preferably an acid/base reaction) which releases a gas.

It is advantageously an acid, a partially salified polyacid salt or a buffer solution of a weak acid and of its conjugate base, or a mixture of such compounds.

According to the invention, the acid/base buffer of said acid may be any acid/base buffer of the weak acid, for instance a citric acid/sodium citrate buffer or a tartaric acid/sodium tartrate buffer. Mention will preferably be made of α-hydroxy acids, which are weak acids preferentially with a pKa of between 2 and 6, such as citric acid, tartaric acid, malic acid or lactic acid, but also phosphoric acid and pyrophosphoric acid and optionally the partially salified salts thereof, such as disodium pyrophosphate or sodium dihydrogen phosphate, also known as monosodium phosphate.

Preferentially, according to the invention, the gas-activating agent is chosen from a tartaric acid/tartrate salt (for example sodium tartrate) buffer; a citric acid/sodium citrate buffer alone; phosphoric acid, monosodium phosphate, disodium pyrophosphate, which are alone or as a mixture with a citric acid/sodium citrate buffer.

According to a very preferred embodiment, the gas-activating agent is a citric acid/sodium citrate buffer, alone or as a mixture with monosodium phosphate and/or disodium pyrophosphate.

In compositions for sensitive skin or for damaged skin, such as acneic skin, the content of citric acid/sodium citrate is preferably less than or equal to 2.4%, relative to the total weight of the intermediate composition A, so as to limit any risk of stinging. In order to improve the tolerance and to avoid the sensation of stinging, preferably, the citric acid/sodium citrate buffer is used as a mixture with disodium pyrophosphate or sodium dihydrogen phosphate.

According to the invention, said gas-activating agent may be present in the intermediate composition A in an amount that may range from 0.001% to 95% by weight relative to the total weight of the intermediate composition A.

Gas-Generating Agent:

The term "gas-generating agent" means any agent which has the property of generating a gas via a chemical reaction. Mention will be made in this regard of any compound which, when it is mixed with a weak acid, can form a gas via a chemical reaction equivalent to the following:

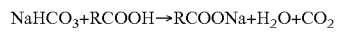

$$NaHCO_3 + RCOOH \rightarrow RCOONa + H_2O + CO_2$$

According to the invention, the gas generated from the gas-generating agent present in the intermediate composition B is preferably carbon dioxide ($CO_2$).

According to the invention, the gas-generating agent is preferably chosen from sodium bicarbonate, potassium bicarbonate, sodium carbonate and potassium carbonate, and mixtures thereof.

Preferentially, according to the invention, the intermediate formulation B comprises an agent which generates carbon dioxide, this agent particularly preferably being sodium bicarbonate.

Said gas-generating agent may be present in the intermediate composition B in an amount ranging from 1% to 10% by weight and preferentially from 2% to 8% by weight, relative to the weight of the intermediate composition B.

According to the invention, the intermediate formulation A may have an acidic pH, advantageously of between 1.0 and 6.0, and the intermediate formulation B may have a basic pH, advantageously of between 7 and 12.

According to the invention, one or both of the intermediate formulations comprise brimonidine, in unmodified form or in salt form, in an amount corresponding to 0.01% to 1% by weight of the brimonidine molecule (i.e. 5-bromoquinoxalin-6-yl)(4,5-dihydro-1H-imidazol-2-yl)amine) relative to the total weight of the total composition.

Preferably, the total composition (mixture of the intermediate formulation A with the intermediate formulation B) contains brimonidine in unmodified form or in salt form, in an amount corresponding to 0.05% to 0.75% by weight, preferentially from 0.09% to 0.6% by weight and more preferentially from 0.1% to 0.5% by weight of the brimonidine molecule, relative to the weight of the total composition.

In the present description, the term "total composition" or "total formulation" means the composition of the product in foam form after said intermediate compositions have been mixed. Brimonidine is preferably contained in intermediate composition A which is more compatible with the active agent.

Brimonidine is preferably used in the form of brimonidine tartrate.

The intermediate formulation A may be in any galenical form that is compatible with the galenical form desired for the final composition obtained by mixing formulation A with formulation B. Advantageously, formulation A may be a gel, a solution, a suspension or an emulsion (cream, surfactant-free cream, lotion, milk or fluid cream), preferably a gel or emulsion containing an aqueous phase in which brimonidine is solubilized.

The intermediate formulation B may be in any galenical form that is compatible with the galenical form desired for the final composition obtained by mixing formulation B with formulation A. Advantageously, formulation B may be a gel, a solution, a suspension or an emulsion (cream, surfactant-free cream, lotion, milk or fluid cream), preferably an emulsion.

According to one embodiment of the invention, one of the two intermediate formulations (i.e. intermediate formulation A or intermediate formulation B) is in the form of a gel. In this embodiment, the other intermediate formulation is preferably not in gel form.

Each intermediate formulation of the kit or of the multi-compartment container as defined previously in accordance with the invention comprises a physiologically acceptable medium which conveys the compound(s) and which is chosen such that the compounds are capable of reacting with each other to form a self-foaming composition during the mixing of at least the intermediate formulations A and B.

Thus, the extemporaneous mixing of at least two formulations, for example formulation A and formulation B, creates the composition in foam form according to the invention.

During the mixing of the two formulations A and B, the gas-generating agent, such as sodium bicarbonate, reacts with the gas-activating agent, such as the acid, and thus gives in particular the salt corresponding to the acid, water and $CO_2$ gas. It is this gas, trapped in the bubbles of the composition, which creates the foam which characterizes the self-foaming composition of the invention.

Thus, by mixing at least intermediate formulation A and intermediate formulation B, the foam composition, referred to as the total composition, according to the invention is obtained. Unreacted gas-activating agent and/or gas-generating agent may, of course, remain in the composition obtained after mixing at least formulations A and B.

Advantageously, the kit or the single multi-compartment container according to the invention may be designed so that, during the preparation of the composition according to the invention, the intermediate formulations A and B can be mixed in an A/B weight ratio ranging from 0.5 to 2, preferentially from 0.5 to 1.5, more preferentially close to 1 (i.e. from 0.9 to 1.1) and even more preferentially 1. This means that the kit can be designed to simultaneously release doses (by weight) of the intermediate compositions A and B that may be in a weight ratio ranging from 2 doses of B per 1 dose of A to 2 doses of A per 1 dose of B, preferably from 2 doses of B per 1 dose of A to 3 doses of A per 2 doses of B. According to a preferred embodiment of the invention, the kit is designed to simultaneously release 1 dose by weight of A and 1 dose by weight of B.

According to the invention, the kit may be in any form that is compatible with, on the one hand, separate storage of the intermediate formulations A and B and, on the other hand, the ability to perform extemporaneous mixing of A and B.

For example, the intermediate formulations A and B may be packaged in a case with at least two separate compartments, each containing A or B.

According to another aspect, the kit may be in the form of a syringe having at least two separate bodies, each equipped with a piston, said two bodies containing the respective formulations A and B and being designed to simultaneously release, by exerting a force on the piston, the desired doses of formulations A and B.

The invention also relates to a process for preparing a composition according to the invention, characterized in that, in order to obtain the composition in foam form, an intermediate formulation A and an intermediate formulation B of the kit as are defined above are mixed extemporaneously in relative weight proportions A/B that may range from 0.5 to 2, preferentially from 0.5 to 1.5 and more preferentially 1.

In order to obtain an optimum foam (final composition), the inventors experimentally sought the optimum contents of gas-generating agent (preferably sodium bicarbonate) and of gas-activating agent (preferably citric acid and/or disodium pyrophosphate and/or sodium dihydrogen phosphate or monosodium phosphate).

Thus, it was determined experimentally that when the gas-activating agent is citric acid, the citric acid/sodium bicarbonate weight ratio is advantageously between 0.1 and 2, preferentially between 0.5 and 1 and very preferably equal to 0.7.

Similarly, it was determined experimentally that when the gas-activating agent is disodium pyrophosphate, the disodium pyrophosphate/sodium bicarbonate weight ratio is between 0.5 and 5, preferentially between 1 and 3 and very preferably equal to 2.4.

Similarly, it was determined experimentally that when the gas-activating agent is sodium dihydrogen phosphate, the sodium dihydrogen phosphate monohydrate/sodium bicarbonate weight ratio is between 0.5 and 5, preferentially between 1 and 3 and very preferably equal to 2.

The sodium bicarbonate/citric acid, sodium bicarbonate/sodium pyrophosphate and sodium bicarbonate/sodium hydrogen phosphate ratios are illustrated in example 4.

Surprisingly, the citric acid/sodium citrate, disodium pyrophosphate or sodium dihydrogen phosphate combination and a gelling system that is compatible with the galenical form made it possible to obtain a formulation with very stable physicochemical properties and in which brimonidine is particularly stable, not giving rise to any unpleasant sensation on the skin and allowing the release of gas and thus the creation of foam.

Example 2B below shows that the compositions according to the present invention have both excellent physical and chemical stability.

A composition is regarded as being physically stable when its organoleptic characteristics, its pH, its viscosity and the homogeneity of brimonidine do not change over time under various temperature conditions: room temperature (RT), 30° C. and 40° C.

According to the invention, room temperature corresponds to a temperature ranging from 15° C. to 25° C.

A composition is regarded as being chemically stable when the content of active principle it contains does not change over time under various temperature conditions (RT and 40° C.). According to the invention, the composition is regarded as being stable when the content of brimonidine (expressed by weight relative to the weight of the intermediate formulation) and measured via any techniques and especially HPLC, is included in the specifications ranging from 90% to 110%.

The composition according to the invention may also comprise one or more agents chosen from dispersants, solubilizers, stabilizers, preserving agents, fatty substances, thickeners, dyes, fragrances, surfactants, gelling agents, complexing agents, neutralizers, non-foaming emulsifying agents, fillers, sequestrants, reducing agents, odor maskers, plasticizers, softeners, moisturizers, pigments, clays, mineral fillers, mineral colloids, polymers, proteins, nacreous agents, waxes, oils, for instance paraffins or silicones, fatty acids, solid esters of fatty alcohols or of fatty acids, gums and wetting agents.

Water-soluble dyes, such as FD&C Blue 1 (of empirical formula $C_{37}H_{34}N_2Na_2O_9S_3$), and liposoluble dyes such as Sudan Red III or Nile Red, have the advantage of coloring one of the formulation intermediates. This coloring makes it possible to monitor the satisfactory mixing of the two formulation intermediates and to highlight the formation of the foam. This coloring is shown in particular in the examples and in FIG. 1.

Gelling Agents for the Intermediate Formulation Comprising the Gas Activator

The intermediate composition A advantageously containing at least one gas-activating agent preferably contains at least one gelling agent and/or suspending agent.

Formulation A may contain large amounts of acid and of electrolytes, said gels being known to be very complicated to stabilize. The viscosity and the suspending power of these formulations are often difficult to ensure over time.

As nonlimiting examples of gelling agents and/or suspending agents which are resistant simultaneously to electrolytes and to acidic pH values and which may be included in the compositions A according to the invention, mention may be made of ready-to-use mixtures, such as the ammonium acrylate/acrylamide copolymer & polyisobutene & polysorbate 20 mixture sold by SEPPIC under the name Sepiplus 265®, the acrylamide/sodium acryloyldimethyl taurate copolymer & isohexadecane & polysorbate 80 mixture sold by SEPPIC under the name Simulgel 600 PHA®, the polyacrylate-13 & polyisobutene & polysorbate 20 mixture sold by SEPPIC under the name Sepiplus 400®, the acrylates/C10-30 alkyl acrylate crosspolymer sold by the company Lubrizol under the names Pemulen™ TR-1 Polymeric Emulsifier and Pemulen™ TR-2 Polymeric Emulsifier polysaccharides with, as nonlimiting examples, xanthan gum, such as Xantural 180® sold by the company Kelco, gellan gum sold under the name Kelcogel® by the company Kelco, sclerotium gum sold under the name Amigel® by Alban Muller Industrie, guar gum and derivatives thereof, such as the hydroxypropyl guar sold under the name Jaguar HP-105® by Rhodia, cellulose and derivatives thereof, such as microcrystalline cellulose and sodium carboxymethyl cellulose sold under the name Blanose CMC 7H4XF® by the company Hercules, hydroxypropylmethylcellulose, in particular the product sold under the name Methocel E4M® Premium by the company Dow Chemical, or hydroxyethylcellulose, in particular the product sold under the name Natrosol HHX 250® by the company Aqualon, the family of the magnesium aluminum silicates, such as Veegum K®, Veegum Plus® or Veegum Ultra® sold by the company Vanderbilt, bentonite sold under the name Polargel HV®, the family of modified starches, such as the modified potato starch sold under the name Structure Solanace®, the family of carrageenans, in particular divided into four main families: κ, λ, β and ω, such as the Viscarin® and Gelcarin® products sold by the company IMCD. Alternatively, polyvinyl alcohol, also known under the abbreviation PVA, sold by Merck under the name Polyvinyl Alcohol 40-88®. Preferably, Veegum K®, Simulgel 600 PHA® and Xantural 180® will be used alone or in combination in pairs or all three together.

The gelling agent as described above may be used at preferential concentrations ranging from 0.001% to 15% and more preferentially ranging from 0.15% to 5% by weight relative to the weight of the intermediate formulation A.

Gelling Agents for the Intermediate Formulation Containing the Gas Generator

As nonlimiting examples of gelling agents and/or suspending agents and/or gelling agents that are simultaneously resistant to electrolytes and two basic pH values and which may be included in the intermediate compositions B according to the invention, mention may be made of acrylic acid polymers such as the acrylates/C10-30 alkyl acrylate crosspolymer such as the "electrolyte-insensitive" carbomers sold under the name Ultrez 20®, Ultrez 10@, Carbopol 1382® or Carbopol ETD2020NF®, Aqua SF1® sold by the company Lubrizol, the ammonium acrylate/acrylamide copolymer & polyisobutene & polysorbate 20 mixture sold by SEPPIC under the name Sepiplus 265®, the acrylamide/sodium acryloyldimethyl taurate copolymer & isohexadecane & polysorbate 80 mixture sold by SEPPIC under the name Simulgel 600 PHA®, the polyacrylates-13 & polyisobutene & polysorbate 20 mixture sold by SEPPIC under the name Sepiplus 400®, the acrylates/C10-30 alkyl acrylate crosspolymer sold by the company Lubrizol under the names Pemulen™ TR-1 Polymeric Emulsifier and Pemulen™ TR-2 Polymeric Emulsifier, polysaccharides with, as nonlimiting examples, xanthan gum, such as Xantural 180® sold by the company Kelco, gellan gum sold under the name Kelcogel® by the company Kelco, sclerotium gum sold under the name Amigel® by Alban Muller Industrie, guar gum and derivatives thereof, such as the hydroxypropyl guar sold under the name Jaguar HP-105® by Rhodia, cellulose and derivatives thereof, such as microcrystalline cellulose and sodium carboxymethyl cellulose sold under the name Blanose CMC 7H4XF® by the company Hercules, hydroxypropylmethylcellulose, in particular the product sold under the name Methocel E4M® Premium by the company Dow Chemical, or hydroxyethylcellulose, in particular the product sold under the name Natrosol HHX 250® by the company Aqualon, bentonite sold under the name Polargel HV®, the family of the magnesium aluminum silicates, such as Veegum K®, Veegum Plus® or Veegum Ultra® sold by the company Vanderbilt, the family of modified starches, such as the modified potato starch sold under the name Structure Solanace® or the tapioca meal known under the name Naviance Tapioca P® sold by AkzoNobel, or the family of carrageenans, in particular divided into four main families: κ, λ, β and ω, such as the Viscarin® and Gelcarin® products sold by the company IMCD. Preferably, Veegum K®, Simulgel 600 PHA® and Xantural 180® will be used alone or in combination in pairs or all three together.

The gelling agent as described above may be used at preferential concentrations ranging from 0.001% to 15% and more preferentially ranging from 0.15% to 5% by weight relative to the weight of the intermediate formulation B.

Humectants

Among the humectants and/or emollients which may act as skin moisturizer and facilitate the application of the formulation, use is optionally made, without this list being limiting, of compounds such as a polyol that is water-miscible at room temperature (25° C.) chosen especially from polyols especially containing from 2 to 20 carbon atoms, preferably containing from 2 to 10 carbon atoms and preferentially containing from 2 to 6 carbon atoms, such as glycerol, glycol derivatives such as propylene glycol, butylene glycol, pentylene glycol, hexylene glycol, dipropylene glycol, diethylene glycol and mixtures thereof, but also sugars (for example glucose or lactose), polyethylene glycols (PEG) (for example Lutrol E400®), urea, and amino acids (for example serine, citrulline, arginine, asparagine or alanine).

As preferred humectant and/or emollient, mention may be made of glycerol and propylene glycol.

The humectants may be used, alone or in combination, at preferential concentrations ranging from 0.001% to 30% and more preferentially ranging from 0.01% to 10% by weight relative to the weight of the total formulation.

Chelating Agents

Among the chelating agents, mention may be made, as nonlimiting examples, of ethylenediaminetetraacetic acid (EDTA), diethylenetriaminepentaacetic acid (DTPA), ethylenediaminebis(O-hydroxyphenylacetic acid) (EDDHA), hydroxy-2-ethylenediaminetriacetic acid (HEDTA), ethyldiaminebis(O-hydroxy-p-methylphenyl)acetic acid (EDDHMA) and ethylenediaminebis(5-carboxy-2-hydroxyphenyl)acetic acid (EDDCHA).

As preferred chelating agent, mention may be made of ethylenediaminetetraacetic acid (EDTA) sold especially under the name Titriplex III®; it may be used at preferential concentrations ranging from 0.001% to 1% and more preferentially from 0.05% to 0.1% by weight relative to the weight of the total formulation.

Excipients with Complementary Properties

The composition according to the invention may contain one or more excipients with specific properties, for instance, as nonlimiting examples, allantoin with anti-irritant properties, dipotassium glycyrrhizate for its anti-inflammatory properties, or alternatively the cicatrizing agent α-bisabolol or lithium digluconate for its anti-redness properties.

Fillers and Particles

Fillers and/or particles may be used to stabilize and boost the foam. Some of them have the specific property of being positioned at the water/air interface and of thus stabilizing this interface. Fillers that may be mentioned include talc, metal oxides such as zinc oxide, titanium dioxide TiO2 T2000 sold by the company Merck under the name Eusolex® T-2000, clays such as laponites, bentones or bentonites, but also cellulose ethers such as Methocel® K100 LV sold by the company Dow, silicas such as Aerosil® R972 sold by the company Evonik or Silice HDK® H13L sold by Wacker; they may be used at concentrations ranging from 0.01% to 10% by weight relative to the weight of the total formulation.

Oils of the Fatty Phase

The composition according to the invention may also comprise a fatty phase. This fatty phase may be present in one and/or the other of the intermediate compositions A and B. Depending on the galenical form of the intermediate formulations, the fatty phase may represent from 0% to 95% by weight relative to the weight of each intermediate formulation.

The fatty phase of the composition according to the invention may comprise, for example, plant, mineral, animal or synthetic oils, silicone oils, and mixtures thereof.

As examples of mineral oils, mention may, for example, be made of liquid paraffins of various viscosities, such as Primol 352®, Marcol 82® and Marcol 152® sold by the company Esso.

As plant oils, mention may be made of sweet almond oil, palm oil, soybean oil, sesame oil, sunflower oil and olive oil.

As animal oils or the substitute thereof of plant origin, mention may be made of lanolin, squalene, fish oil with, as a derivative, the perhydrosqualene sold under the name Sophiderm® by the company Sophim.

As synthetic oils, mention may be made of an ester such as cetearyl isononanoate, for instance the product sold under the name Cetiol SN PH® by the company Cognis France, isononyl isononanoate such as Dub ININ® sold by the company Stéarineries Dubois, diisopropyl adipate, for instance the product sold under the name Crodamol DA® by the company Croda, isopropyl palmitate, for instance the product sold under the name Crodamol IPP® by the company Croda, and caprylic/capric triglyceride, such as Miglyol 812® sold by the company Univar. As hydrogenated polyisobutenes, mention may be made of the Parleam® products sold by the company Rossow.

As silicone oils, mention may be made of a dimethicone, for instance the product sold under the name Q7-9120 Silicone Fluid® with a viscosity from 20 cSt to 12 500 cSt, by the company Dow Corning, or a cyclomethicone, for instance the product sold under the name ST-Cyclomethicone 5NF®, also by the company Dow Corning.

Nonliquid Fatty Substances

The composition according to the invention, and in particular the intermediate formulation B, may also comprise solid fatty substances such as natural or synthetic waxes, fatty acids such as stearic acid, fatty alcohols such as Speziol C18® Pharma or Speziol C16® sold by the company Cognis, and texturing agents of tribehenate type, such as Compritol 888® sold by the company Gattefossé or hydrogenated castor oils such as Cutina HR® sold by the company Cognis or glyceryl stearate such as Geleol® sold by the company Gattefossé or DC 9045 Elastomer Blend® sold by the company Dow Corning.

These nonliquid fatty substances may be used alone or as a mixture from 0% to 30% by weight relative to the weight of the total formulation. However, exceptional foam quality has been observed when fatty alcohols of formula CH3 (CH2)nOH (n is between 11 and 23) are present in contents of greater than 1% by weight relative to the weight of the total formulation.

Nonionic Emulsifiers

The composition according to the invention, and especially the intermediate formulation B, may also comprise one or more nonionic emulsifiers.

Preferred emulsifiers that may be mentioned include hydrophilic emulsifiers such as glyceryl stearate (and) PEG-100 stearate sold under the name Arlacel 165FL® by the company Uniqema, lipophilic emulsifiers such as Glucate SS® and Glucamate SSE®, polyoxyethylene (21) stearyl ether sold under the name Brij 721® by the company Uniqema or also in the same family Brij S2® and Brij S20®. The self-emulsifying wax sold by Croda under the name of Polawax NF®. Mention may also made of nonionic surfactants with a high HLB, sorbitan esters such as POE(20) sorbitan monooleate sold under the name Tween 80® (HLB=15), POE(20) sorbitan monostearate sold under the name Tween 60® (HLB=14.9), fatty alcohol ethers such as POE (21) stearyl ether (HLB=15.5), or ceteareth-20 sold under the name of Eumulgin B2 PH® by Cognis (HLB of 15.5), or nonionic surfactants with a low HLB, sorbitan esters, such as sorbitan monostearate (sold under the name of Span 60® by Uniqema), glycerol esters such as glyceryl monostearate (Cutina GMS® from Cognis), sucrose esters with a low HLB, such as sucrose distearate. In another form according to the invention, the surfactants that may be used are polyglycerol esters. They are esters of polyglycerolated fatty acids obtained by condensation of glycerol. Glycolipid emulsifiers, such as Montanov 202® sold by the company SEPPIC. Some emulsifiers may be sold in the form of a mixture, such as Emulium Kappa® and Emulium Delta® sold by Gattefossé. These surfactants may be used, alone or as a mixture, so that the HLB of the system is greater than 12 and preferentially greater than 15.

Such emulsifiers may be used at between 0.01% and 30% by weight, relative to the weight of the total composition, preferentially between 0.1% and 15% and more preferentially between 0.5% and 7%.

Preserving Agents

Examples of preserving agents that may be mentioned include benzalkonium chloride, bronopol, chlorhexidine, chlorocresol and derivatives thereof, ethyl alcohol, phenoxyethanol, potassium sorbate, diazolidinyl urea, benzyl alcohol, parabens and sodium benzoate, or mixtures thereof.

As preferred preserving system, mention may be made of combining phenoxyethanol and pentylene glycol.

The examples that follow illustrate the invention without limiting its scope.

EXAMPLES

Example 1: Formulation Examples

Formulation Examples A: Intermediate Compositions a Containing the Gas-Activating Agent Intermediate formulations A were prepared according to the following process:

Step 1: At a temperature above 60° C., add the main gelling agent (Veegum K) with stirring to the main water phase.

Step 2: Add the acidic buffer agents and then cool to 40° C.

Step 3: With magnetic stirring, dissolve the brimonidine in the remaining additional aqueous phase. Transfer this additional phase into the main phase.

Step 4: Add the other gelling agent(s) with stirring.

Step 5: Add the other excipients of the formulation with stirring.

In the formulation examples below, the amounts are expressed relative to the weight of the intermediate formulation rather than relative to the weight of the total formulation.

Example A1

| INCI Name | Weight % |
| --- | --- |
| WATER | QS 100 |
| DISODIUM EDTA | 0.1 |
| MAGNESIUM ALUMINIUM SILICATE | 2.5 |
| XANTHAN GUM | 1.5 |
| CITRIC ACID | 1.4 |
| SODIUM CITRATE | 1 |
| DISODIUM PYROPHOSPHATE | 7.2 |
| POLOXAMER 124 | 0.2 |
| PROPYLENE GLYCOL | 4 |
| SODIUM BENZOATE | 0.2 |
| BRIMONIDINE TARTRATE | 1 |

Example A2

| INCI Name | Weight % |
| --- | --- |
| WATER | QS 100 |
| DISODIUM EDTA | 0.1 |
| MAGNESIUM ALUMINUM SILICATE | 2.5 |
| XANTHAN GUM | 1.5 |
| CITRIC ACID | 3.5 |
| SODIUM CITRATE | 2.7 |
| PROPYLENE GLYCOL | 4 |
| SODIUM BENZOATE | 0.2 |
| BRIMONIDINE TARTRATE | 1 |

Example A3

| INCI Name | Weight % |
| --- | --- |
| WATER | QS 100 |
| DISODIUM EDTA | 0.1 |
| MAGNESIUM ALUMINUM SILICATE | 2.5 |
| XANTHAN GUM | 1.5 |
| CITRIC ACID | 1.5 |
| SODIUM CITRATE | 0.5 |
| SODIUM DIHYDROGEN PHOSPHATE | 6.2 |
| PROPYLENE GLYCOL | 4 |
| SODIUM BENZOATE | 0.2 |
| BRIMONIDINE TARTRATE | 1 |

Example A4

| INCI Name | Weight % |
| --- | --- |
| WATER | QS 100 |
| DISODIUM EDTA | 0.1 |
| MAGNESIUM ALUMINUM SILICATE | 2.5 |
| XANTHAN GUM | 1.5 |
| CITRIC ACID | 1.5 |
| SODIUM CITRATE | 0.5 |
| SODIUM DIHYDROGEN PHOSPHATE | 6.2 |
| PROPYLENE GLYCOL | 4 |
| SODIUM BENZOATE | 0.2 |
| BRIMONIDINE TARTRATE | 0.36 |

Example A5

| INCI Name | Weight % |
| --- | --- |
| WATER | QS 100 |
| DISODIUM EDTA | 0.1 |
| XANTHAN GUM | 0.7 |
| MAGNESIUM ALUMINUM SILICATE | 2.5 |
| DISODIUM PYROPHOSPHATE | 6 |
| CITRIC ACID | 1.8 |
| SODIUM CITRATE | 1.3 |
| POLOXAMER 124 | 0.2 |
| BRIMONIDINE TARTRATE | 1 |
| PROPYLENE GLYCOL | 4.0 |

Example A7

| INCI Name | Weight % |
| --- | --- |
| WATER | QS 100 |
| DISODIUM EDTA | 0.1 |
| XANTHAN GUM | 0.7 |
| MAGNESIUM ALUMINIUM SILICATE | 2.5 |
| SODIUM BENZOATE | 0.2 |
| DISODIUM PYROPHOSPHATE | 7.2 |
| CITRIC ACID | 1.4 |
| SODIUM CITRATE | 1 |
| POLOXAMER 124 | 0.2 |
| BRIMONIDINE TARTRATE | 1 |
| PROPYLENE GLYCOL | 4.0 |

Formulation B: Intermediate Compositions B Comprising the Gas-Generating Agent

The intermediate formulations B were prepared according to the following process:

Step 1': At a temperature above 60° C., add the gelling agents with stirring to the main water phase.

Optional step 2': In parallel, heat the fatty phase (containing the oils, the waxes and the surfactants) to a temperature above 60° C.

Step 3' I: At a temperature above 60° C., prepare the emulsion by adding the fatty phase to the main phase.

Step 4': Add the additives such as the preserving agents or ethanol at a temperature suitable for the additive.

Step 5': Neutralize the mixture.

Step 6': At a temperature below 40° C., add the sodium bicarbonate.

Example B1

| INCI Name | Weight % |
| --- | --- |
| WATER | QS 100 |
| MAGNESIUM ALUMINUM SILICATE | 2.5 |
| XANTHAN GUM | 0.6 |
| POLYSORBATE 80 | 0.8 |
| STEARETH-20 | 2.8 |
| CETOSTEARYL ALCOHOL | 1.5 |
| MINERAL OIL | 8 |
| TRIETHANOLAMINE | 1.2 |
| SODIUM HYDROGEN CARBONATE | 5 |

Examples B2 and B3

| INCI NAME | Weight B2 % | Weight B3 % |
| --- | --- | --- |
| WATER | QS 100 | QS 100 |
| SODIUM CARBOXYMETHYLCELLULOSE | 0.5 | 0.2 |
| HYDROXYETHYLCELLULOSE | 1 | 0.1 |
| STEARETH-20 | 1.8 | 1.8 |
| GLYCERYL STEARATE (AND) PEG-100 STEARATE | 2.7 | 2.7 |
| CETOSTEARYL ALCOHOL | 1 | 7 |
| HYDROGENATED POLYISOBUTENE | 9 | 9 |
| TRIETHANOLAMINE | 1.2 | 1.2 |
| PROPYLENE GLYCOL | 5 | 5 |
| PHENOXYETHANOL | 1 | 1 |
| SODIUM HYDROGEN CARBONATE | 3 | 3 |

Example B5

| INCI Name | Weight % |
| --- | --- |
| WATER | QS 100 |
| MAGNESIUM ALUMINUM SILICATE | 3.5 |
| XANTHAN GUM | 1 |
| POLYSORBATE 80 | 2 |
| STEARIC ACID | 3 |
| CETOSTEARYL ALCOHOL | 1.5 |
| HYDROGENATED POLYISOBUTENE | 8 |
| TRIETHANOLAMINE | 1.8 |
| SODIUM HYDROGEN CARBONATE | 3 |
| PHENOXYETHANOL | 0.8 |

Example B6

| INCI Name | Weight % |
| --- | --- |
| WATER | QS 100 |
| MAGNESIUM ALUMINUM SILICATE | 2.5 |
| XANTHAN GUM | 0.6 |
| CETEARETH-20 | 3 |
| CAPRYLIC/CAPRIC TRIGLYCERIDE | 6 |
| CETOSTEARYL ALCOHOL | 7 |
| TRIETHANOLAMINE | 0.1 |
| SODIUM HYDROGEN CARBONATE | 5 |
| PHENOXYETHANOL | 0.8 |

Example B7

| INCI Name | % |
| --- | --- |
| WATER | QS 100 |
| MAGNESIUM ALUMINUM SILICATE | 2.5 |
| XANTHAN GUM | 0.5 |
| CETEARETH-20 | 3 |
| CETOSTEARYL ALCOHOL | 3 |
| GLYCERYL DIBEHENATE | 3 |
| CAPRYLIC/CAPRIC TRIGLYCERIDE | 6 |
| SODIUM HYDROXYDE | 0.09 |
| PHENOXYETHANOL | 0.8 |
| SODIUM HYDROGEN CARBONATE | 5 |

The mixtures in a 1:1 weight ratio of the intermediate compositions A and B described above are represented in the table below. A cross at the intersection of two formulation intermediates indicates that the mixture was tested and generated a foam having the desired properties.

| | Formulation B | | | | | |
| --- | --- | --- | --- | --- | --- | --- |
| Formulation A | B1 | B2 | B3 | B5 | B6 | B7 |
| A1 | X | X | X | X | X | X |
| A2 | X | X | X | X | X | X |
| A3 | X | X | X | X | X | X |
| A5 | X | X | X | X | X | X |

-continued

| | Formulation B | | | | | |
|---|---|---|---|---|---|---|
| Formulation A | B1 | B2 | B3 | B5 | B6 | B7 |
| A4 | X | X | X | X | X | X |
| A7 | X | X | X | X | X | X |

Example 2A: Foam Density Measurements

From the formulation examples described in example 1, foam density measurements were taken at the time of placing in contact of the two intermediate formulations A and B (T0) and then when the chemical reaction generated by the placing in contact of the two compositions is complete:

Density placebo formulation A5, i.e. without brimonidine (but with blue colorant)=1.108
  Density formulation B7=1.021
  Foam A5/B7 (50/50)=0.290

The foam density measurement shows that the volume increased by a factor of 4 and was confirmed by the photographs in FIG. 1. The left-hand photo represents the moment of mixing (T0) and the right-hand photo represents the foam obtained when the acid/base chemical reaction is complete.

Example 2B: Stability

Tables Ia and Ib below collate the physical stability data of the intermediate formulations A1 and A3 described in example 1, containing brimonidine.

| | T0 | | T1 Month | T2 Months | T3 Months | T6 Months |
|---|---|---|---|---|---|---|
| Formulation A1 | | | | | | |
| pH | 3.99 | RT | 4.11 | 4.15 | 4.18 | 4.06 |
| | | 5° C. | 4.02 | 4.09 | — | — |
| | | 40° C. | 4.16 | 4.17 | — | 4.11 |
| Viscosity cP Brookfield RV DVII spindle 5 speed 50 | 6200 | RT | 6020 | 5880 | — | 6900 |
| | | 40° C. | 5600 | 5710 | — | 5600 |
| Formulation A3 | | | | | | |
| pH | 3.46 | RT | 3.83 | 3.85 | 3.84 | 3.87 |
| | | 5° C. | 3.69 | 3.67 | 3.64 | 4.15 |
| | | 40° C. | 3.98 | 3.91 | 3.93 | 3.99 |
| Viscosity cP Brookfield LV DVII spindle 63 speed 20 | 14219 | RT | 13027 | 18877 | 11600 | 10648 |
| | | 5° C. | 13400 | 14150 | 11338 | 10708 |
| | | 40° C. | 14999 | 13407 | 12567 | 10588 |

Table II below details the chemical stability data for brimonidine in the intermediate formulation A1.

| Formulation A1 | T0 | | T1 Month | T2 Months | T3 Months |
|---|---|---|---|---|---|
| wt %/BRIMONIDINE (HPLC) | 97.4 | RT | 97.3 | 96.3 | 98.9 |
| | | 40° C. | 97.5 | 96.2 | 99.2 |

Example 3: Comparative Study of Measurement of Irritation

Study Protocol.

The study is performed according to the OECD TG 439 protocol in force for the short application time (RHE/product contact time 15 min). This protocol is appropriate for a long application time (RHE/product contact time 18 h).

The objective of this study is to evaluate the tolerance of the supports of the complete and intermediate formulations on reconstructed human epidermides (RHE, Episkin model) through:
  evaluation of the reduction of MTT (cell viability)
  measurement of the release of IL-1alpha (irritation marker)
The formulations tested are:
  An intermediate composition of acidic formulation: placebo example A7 (i.e. not containing brimonidine),
  An intermediate composition of basic formulation: example B7,
  The complete formulation composed of the mixture: A7 placebo+B7 (in a 50/50 weight ratio),
  A commercial reference in cream form.

Study Results:

| Mixture tested | Short exposure Viability (%) | Long exposure Viability (%) | Conclusion Irritant potential |
|---|---|---|---|
| B7 | 89.8 | 93.3 | Non-irritant |
| A7 placebo | 86.0 | 84.5 | Non-irritant |
| Complete formulation | 95.8 | 83.4 | Non-irritant |
| Commercial ref. | 99.8 | 91.1 | Non-irritant |

| Mixture tested | Short exposure IL-1a vs control | Long exposure IL-1a vs control |
|---|---|---|
| B7 | 1.5 | 2.0 |
| A7 placebo | 2.2 | 2.3 |
| Complete formulation | 1.9 | 3.1 |
| Commercial ref. | 2.4 | 3.6 |

The MTT measurements according to the OECD protocol in force indicate that all the formulations tested are non-irritant.

The assay of IL-1a of the complete formulation according to the invention after a short exposure time and a long exposure time shows a lower content of irritation markers than after application of the commercial reference.

Example 4

The ideal content of citric acid, sodium pyrophosphate and sodium dihydrogen phosphate monohydrate to react with 5% of sodium bicarbonate was established empirically. The values are expressed as weight/weight percentages relative to the weight of each of the two intermediate formulations.

|  | Ratio 1 | Ratio 2 | Ratio 3 |
|---|---|---|---|
| Sodium bicarbonate | 5% | 5% | 5% |
| Citric acid | 3.5% | — | — |
| Disodium pyrophosphate | — | 12 | — |
| Sodium dihydrogen phosphate monohydrate | — | — | 7.2% |

In order for the pH of the formulation containing the gas activator to have optimum compatibility with the skin, sodium citrate was added so as to create a citric acid/sodium citrate buffer.

Part of the citric acid/sodium citrate buffer may advantageously be replaced with disodium pyrophosphate and vice versa like the contents cited by way of example in the table below:

Table III: the values are expressed as weight/weight percentages relative to the weight of each of the two intermediate formulations.

|  | E1 | E2 | E3 | E4 | E5 | E6 | E7 |
|---|---|---|---|---|---|---|---|
| Sodium bicarbonate | 5% | 5% | 5% | 5% | 3% | 3% | 3% |
| Citric acid | 3.5% | 1.75% | 1.4% | 0 | 2.1% | 1.05% | 0 |
| Sodium citrate | 2.7% | 1.3% | 1% | 0 | 1.6% | 1.15% | 0 |
| Disodium pyrophosphate | 0 | 6% | 7.2% | 12% | 0 | 3.6% | 7.2% |

Part of the citric acid/sodium citrate buffer may advantageously be replaced with sodium dihydrogen phosphate monohydrate and vice versa, like the contents cited by way of example in table IV below:

Table IV: the values are expressed as weight/weight percentages relative to the weight of each of the two intermediate formulations.

|  | E1 | E8 | E9 |
|---|---|---|---|
| Sodium bicarbonate | 5% | 5% | 5% |
| Citric acid | 3.5% | 1.5% | 0 |
| Sodium citrate | 2.7% | 0.5% | 0 |
| Sodium dihydrogen phosphate monohydrate | 0 | 6.2% | 10% |

In one particular embodiment, it was determined that when the amount of citric acid is greater than or equal to 1.4, the amount of foam is optimal when disodium pyrophosphate is present in the composition according to the following equation:

$$[C] = 2.4[B] - 2.4[A]/0.7$$

when:

[C]=weight content of disodium pyrophosphate in the intermediate composition A

[A]=weight content of citric acid monohydrate in the intermediate composition A

[B]=weight content of sodium bicarbonate in the intermediate composition B

The above equation thus makes it possible to calculate the optimum contents between sodium bicarbonate, citric acid and sodium pyrophosphate.

Example 5: Comparative Study of Release Profile-Permeation

Study Protocol:

The formulations tested in this study are applied to excised whole human skin samples mounted on a Franz cell at a rate of 5 mg/cm$^2$ at 32° C.

After 16 hours of application, brimonidine tartrate is assayed in: the fraction not absorbed, the stratum corneum, the epidermis, the dermis and the receiver fluid.

This study makes it possible to study the influence of the formulation on the release of the active principle and its permeation through the skin. The object is to compare the distribution of brimonidine tartrate in the various skin layers in the event of the application of a reference formulation and the application of a composition in chemical foam form.

The formulations tested are:
- a reference commercial composition containing 0.33% by weight of brimonidine in base form corresponding to 0.5% by weight of brimonidine tartrate;
- a reference in gel form containing 0.12% by weight of brimonidine in base form corresponding to 0.18% by weight of brimonidine tartrate;
- a foam formulation according to the invention containing 0.5% by weight of brimonidine tartrate (i.e. 0.33% by weight of brimonidine) composed of the mixture of compositions A3 and B7 of example 1 (in a 50/50 weight ratio);
- a foam formulation according to the invention containing 0.18% by weight of brimonidine tartrate (i.e. 0.12% by weight of brimonidine) composed of the mixture of compositions A4 and B7 of example 1 (in a 50/50 weight ratio).

Diffusion Cells:

The diffusion cells used are static diffusion cells, on the basis of the Franz model diffusion cell, with the following characteristics:

Application area=2 cm$^2$

Volume of the receiver fluid compartment=3 ml

The receiver compartment is surrounded by a water jacket heated at 37° C.±1° C. to ensure a temperature of 32° C.±1° C. at the skin surface. The receiver compartment is separated from the donor compartment by the skin membrane, the epidermal face being on the donor side. The receiver compartment containing a magnetic stirring bar was filled with the receiver fluid so as to prevent any formation of air bubbles. During the diffusion time, the receiver fluid was stirred continuously so as to ensure homogenization.

Preparation of the Skin Samples:

Abdominal skin samples derived from cosmetic surgery were used in this study. On arrival of the samples, the hypodermis was separated from the assembly using tweezers, and the remaining material was washed gently and stored flat in aluminum foil for storage at −20° C. On the day of the experiment, the skin samples were thawed and then cut into pieces to be compatible with the geometry of the diffusion cell.

The skin samples, derived from donors 42, 44 and 69 years old, were mounted on the diffusion cell with PBS as receiver fluid. The mean skin thickness was 0.89±0.07 mm with a maximum of 1.39 mm and a minimum of 0.45 mm. Thicknesses of all the specimens.

After at least 45 minutes at equilibrium with the receiver fluid, the skin integrity was evaluated by measuring the trans-epidermal water loss (TEWL). All the cells whose TEWL measurements were outside the acceptance criteria are carefully cleaned and left at equilibrium for a prolonged period before remeasuring the TEWL. The mean TEWL value was 5.51±1.63 g/m$^2$/h.

Study Parameters:
  Room temperature: 21.7° C.
  Relative humidity 45.6%

Study Results:

In the stratum corneum and in the epidermis a difference in skin penetration was observed between the foam formulations of the invention containing 0.18% of brimonidine tartrate composed of the mixture of compositions A4 and B7 (in a 50/50 weight ratio) compared to a reference gel containing 0.18% of brimonidine tartrate) as described in FIG. 2A. In the stratum corneum, a significant difference in skin penetration was observed between the foam formulations of the invention containing 0.5% of brimonidine tartrate composed of the mixture of compositions A3 and B7 (in a 50/50 weight ratio) and the reference gel product containing 0.5% of brimonidine tartrate as described in FIG. 3A. A difference was also observed under the same conditions in the epidermis as described in FIG. 3A.

In the dermis, the differences between the chemical foams and the reference gel forms tended to be reduced. No significant difference was observed between the two forms for the two concentrations tested as illustrated in FIGS. 2B and 3B. Moreover, no significant difference was found between the concentrations tested in the same form (no dose effect) suggesting that the variability of the data prevents the statistical significance (ANOVA test F (3, 8)=1.46, P=0.296).

The present study confirms the production of a foam which remains on the surface of the skin and delivers a smaller amount so as to avoid adverse effects (rebound effect) and to obtain a foam that is suitable for treating rosacea.

The invention claimed is:

1. A self-foaming composition formulated for leave-on topical application, separately comprising:
   (a) at least one intermediate composition B comprising: (i) a gas-generating agent, (ii) 0.15% to 5% by weight, relative to the weight of composition B, of gelling agents, and (iii) a fatty phase comprising 1% to 30% by weight, relative to the total weight of the composition, of one or more fatty alcohols of the formula CH$_3$(CH$_2$)$_n$OH, wherein n is between 11 and 23;
   (b) at least one intermediate composition A comprising: (i) an agent for activating the gas-generating agent, and (ii) 0.15% to 5% by weight, relative to the weight of composition A, of gelling agents; and
   (c) brimonidine or a pharmaceutically acceptable salt thereof,
   wherein the brimonidine or pharmaceutically acceptable salt thereof is present in intermediate composition(s) A and/or B;
   wherein the gelling agents do not comprise cellulose or cellulose derivatives; and
   wherein intermediate compositions A and B generate gas upon mixing with one another.

2. The composition of claim 1, wherein the brimonidine is present in the intermediate composition A.

3. The composition of claim 1, wherein the composition does not comprise any foaming surfactants selected from the group consisting of anionic surfactants, cationic surfactants, amphoteric surfactants and nonionic surfactants of the family of alkylpolyglucosides and glucamides.

4. The composition of claim 1, wherein the gas generated from the gas-generating agent is carbon dioxide.

5. The composition of claim 1, wherein the gas-generating agent is selected from the group consisting of sodium bicarbonate, potassium bicarbonate, sodium carbonate and potassium carbonate, and mixtures thereof.

6. The composition of claim 1, wherein the gas-generating agent is present in the intermediate composition B in an amount ranging from 1% to 10% by weight, relative to the weight of the intermediate composition B.

7. The composition of claim 1, wherein the intermediate composition B has a pH of from 7 to 12.

8. The composition of claim 1, wherein the agent for activating the gas-generating agent is selected from the group consisting of an acid, a partially salified polyacid salt, a buffer solution of a weak acid and of its conjugate base, and mixtures of these compounds.

9. The composition of claim 1, wherein the agent for activating the gas-generating agent is selected from the group consisting of citric acid, tartaric acid, malic acid, lactic acid, phosphoric acid and pyrophosphoric acid, and salts of these acids.

10. The composition of claim 1, wherein the agent for activating the gas-generating agent is a citric acid/sodium citrate buffer, alone or as a mixture with sodium phosphate and/or disodium pyrophosphate.

11. The composition of claim 1, wherein the agent for activating the gas-generating agent is present in the intermediate composition A in an amount ranging from 0.001% to 95% by weight, relative to the weight of the intermediate composition A.

12. The composition of claim 1, wherein the intermediate composition A has an acidic pH.

13. The composition of claim 1, wherein the intermediate composition A is in the form of a solution, a gel, or an emulsion.

14. The composition of claim 1, wherein the intermediate composition B is in the form of a solution, a gel, or an emulsion.

15. The composition of claim 1, wherein the brimonidine or pharmaceutically acceptable salt thereof is brimonidine tartrate.

16. A composition in foam form, wherein the composition is obtained by mixing the intermediate compositions A and B, as defined in claim 1.

17. The composition of claim 1, wherein the composition further comprises one or more active agents selected from the group consisting of emollients, humectants, free-radical scavengers, anti-inflammatory agents, vitamins, depigmenting agents, antiacne agents, antiseborrheic agents, antifungal agents, keratolytic agents, sunscreens, slimming agents and skin-coloring agents.

18. The composition of claim 1, wherein the composition further comprises one or more agents selected from the group consisting of dispersants, solubilizers, stabilizers, preserving agents, fatty substances, thickeners, dyes, fragrances, gelling agents, complexing agents, neutralizers, non-foaming emulsifying agents, fillers, sequestrants, reducing agents, odor maskers, plasticizers, softeners, moisturizers, pigments, clays, mineral fillers, mineral colloids, polymers, proteins, nacreous agents, propellants, waxes, oils, for instance paraffins, fatty acids, solid esters of fatty alcohols or of fatty acids, gums and wetting agents.

19. A cosmetic method comprising topically administering the composition of claim 1, to the skin of an individual subject in need thereof.

20. A kit or single multi-compartment container separately comprising:
  (a) at least one intermediate composition B comprising: (i) at least one gas-generating agent, (ii) 0.15% to 5% by weight, relative to the weight of composition B, of gelling agents, and (iii) a fatty phase comprising 1% to 30% by weight, relative to the total weight of the composition, of one or more fatty alcohols of the formula $CH_3(CH_2)_nOH$, wherein n is between 11 and 23;
  (b) at least one intermediate composition A comprising: (i) at least one agent for activating the gas-generating agent, and (ii) 0.15% to 5% by weight, relative to the weight of composition A, of gelling agents; and
  (c) brimonidine or a pharmaceutically acceptable salt thereof,
  wherein the brimonidine or a pharmaceutically acceptable salt thereof is present in intermediate composition(s) A and/or B;
  wherein the gelling agents do not comprise cellulose or cellulose derivatives; and
  wherein intermediate compositions A and B generate gas upon mixing with one another.

21. The kit or container of claim 20, wherein the kit or container is designed for mixing the intermediate compositions A and B in an A/B weight ratio ranging from 0.5 to 2.

22. A process for preparing a composition in foam form, comprising formulating the composition for leave-on topical application by mixing the intermediate composition A as defined in claim 1 with the intermediate composition B as defined in claim 1, in a relative weight proportion A/B ranging from 0.5 to 2, wherein brimonidine or a pharmaceutically acceptable salt thereof is present in at least one of intermediate compositions A and B.

23. The composition of claim 3, wherein the composition does not comprise any foaming surfactants.

24. The composition of claim 5, wherein the gas-generating agent is sodium bicarbonate.

25. The composition of claim 6, wherein the gas-generating agent is present in the intermediate composition B in an amount ranging from 2% to 8% by weight.

26. The composition of claim 7, wherein the pH is a basic pH.

27. The composition of claim 9, wherein the agent for activating the gas-generating agent is selected from the group consisting of: a tartaric acid/tartrate salt buffer; a citric acid/sodium citrate buffer alone; and phosphoric acid, sodium phosphate, and/or disodium pyrophosphate, which are alone or as a mixture with a citric acid/sodium citrate buffer.

28. The composition of claim 12, wherein the acidic pH is from 1.0 to 6.0.

29. The kit or container of claim 21, wherein the A/B weight ratio ranges from 0.5 to 1.5.

30. The kit or container of claim 21, wherein the A/B weight ratio ranges from 0.9 to 1.1.

31. The kit or container of claim 21, wherein the A/B weight ratio is 1.

32. The process of claim 22, wherein the A/B weight proportion is from 0.5 to 1.5.

33. The process of claim 22, wherein the A/B weight proportion is 1.

\* \* \* \* \*